United States Patent
Okubo et al.

(10) Patent No.: US 6,632,494 B1
(45) Date of Patent: Oct. 14, 2003

(54) HIGHLY ABSORBENT RESIN, ABSORBENT ARTICLE, DISPOSAL BAG OR PACKAGING MATERIAL OF HIGHLY ABSORBENT RESIN OR ABSORBENT ARTICLE, PACKAGE OF HIGHLY ABSORBENT RESIN OR ABSORBENT ARTICLE, AND METHOD FOR INCINERATING HIGHLY ABSORBENT RESIN OR ABSORBENT ARTICLE

(75) Inventors: Toshiya Okubo, Kagawa (JP); Yoshiko Yamamoto, Kagawa (JP); Shoko Hayakawa, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/429,544

(22) Filed: Oct. 28, 1999

(30) Foreign Application Priority Data

Nov. 2, 1998 (JP) ............................................ 10-311745

(51) Int. Cl.⁷ ............................... B32B 1/00; B65F 5/00
(52) U.S. Cl. .................. 428/35.7; 428/35.9; 428/35.2; 428/36.9; 604/385.1
(58) Field of Search ................. 428/35.2, 35.7, 428/35.9, 36.9; 604/385.1

(56) References Cited

U.S. PATENT DOCUMENTS 4,090,013 A * 5/1978 Ganslaw ...................... 526/15
4,425,856 A * 1/1984 Szilagyi ...................... 110/346
5,141,505 A * 8/1992 Barrett ....................... 604/385.1

FOREIGN PATENT DOCUMENTS

| EP | 0808563 | * 11/1997 |
| GB | 2082614 | * 3/1982 |
| JP | 54-1976 | 1/1979 |
| JP | 3-67553 | 10/1991 |
| JP | 07203793 | * 8/1995 |

* cited by examiner

Primary Examiner—Harold Pyon
Assistant Examiner—Marc Patterson
(74) Attorney, Agent, or Firm—Darby & Darby

(57) ABSTRACT

The invention provides a highly absorbent resin including a polyvalent metal compound capable of preventing the melting and solidification of the highly absorbent resin and the deposition thereof on the wall of an incinerator during the incineration and disposal of the highly absorbent resin; an absorbent article including the highly absorbent resin and the polyvalent metal compound; a disposal bag or packaging material of the highly absorbent resin or the absorbent article, the disposal bag or packaging material including the polyvalent metal compound; a package of the highly absorbent resin or the absorbent article, packing the polyvalent metal compound therewith; and a method for incinerating and disposing the highly absorbent resin or the absorbent article by adding the polyvalent metal compound.

26 Claims, 1 Drawing Sheet

HIGHLY ABSORBENT RESIN, ABSORBENT ARTICLE, DISPOSAL BAG OR PACKAGING MATERIAL OF HIGHLY ABSORBENT RESIN OR ABSORBENT ARTICLE, PACKAGE OF HIGHLY ABSORBENT RESIN OR ABSORBENT ARTICLE, AND METHOD FOR INCINERATING HIGHLY ABSORBENT RESIN OR ABSORBENT ARTICLE

FIELD OF THE INVENTION

The present invention relates to a method for incineration for the disposal of a highly absorbent resin or a hydrophilic polymer electrolyte of a crosslinked structure, specifically an alkali metal salt thereof, and various absorbent articles comprising the above, with out the occurrence of any problem.

BACKGROUND OF THE INVENTION

Absorbent articles, including disposable diaper, sanitary napkin or the like, comprise fluff pulp and highly absorbent resins as absorbent materials. Due to sanitary and hygienic concerns, conventionally, these absorbent articles have been incinerated and disposed after use, because these absorbent articles have been used to absorb urine or menstrual blood. However, although the fluff pulp dose not raise particular problems during incineration and disposal, the incineration and disposal of highly absorbent resins in the absorbent articles is potentially problematic as follows;
1. High ash content after incineration.
Ash content of fluff pulp incinerated at a high temperature, e.g., 800° C. for 2 hours is about 0.1 wt %, while that of a highly absorbent acrylic resin is 40 to 60 wt %.
2. Alkaline ash.
Highly absorbent resins are generally in the forms of alkali metal salts of polymers, particularly sodium salts and potassium salts of polymers.
3. Highly absorbent resins are readily solidified into rubbery state after incineration.
4. During and after incineration, highly absorbent resins or the resulting ash readily attach to the incinerator wall or base, after which they are difficult to remove.
5. Highly absorbent resins damage the inside of the incinerator (because of the properties described above in 1 to 4).

These hidden problems have not been clearly recognized, so that currently, absorbent articles comprising highly absorbent resins are still mainly disposed of through incineration.

Nevertheless, the problems may well be addressed in near future because of the following reasons.
1. Because the thickness and weight of absorbent articles are being downsized of their and because the ratio of the cost of highly absorbent resins to the cost of pulp is being reduced, the ratio of highly absorbent resins is likely to increase in new absorbent articles while the ratio of fluff pulp therein is likely to decrease.
2. Due to the spread of disposable diaper usage among aged people, the ratio of absorbent articles or highly absorbent resins to the total amount of wastes to be incinerated is likely to increase.
3. Because the volume of wastes to be incinerated is likely to decrease due to the enforcement of the Container and Package Law Recycling, the ratio of the absorbent articles or highly absorbent resins to the total amount of wastes to be incinerated will likely increase.
4. Wastes from institutions for aged individuals and hospitals are often incinerated in these institutions' own equipment. The ratio of the absorbent articles or highly absorbent resins to the wastes to be incinerated by this equipment is higher than the ratio thereof for general wastes.

To overcome these problems, no effective means has been established from the side of suppliers of highly absorbent resins and absorbent articles. At present, measures to improve the function of incinerators or to apply various maintenance strategies at incineration sites, have been relied upon.

SUMMARY OF THE INVENTION

In accordance with the invention, a means is provided for dealing directly with highly absorbent resins and absorbent articles, wherein among the problems involved in the incineration of these absorbent resins, the means can overcome the problem causing the incinerator damage due to the deposition inside the incinerator.

It is an object of the invention to provide a highly absorbent resin or an absorbent article comprising the highly absorbent resin, whereby the melting and solidification of the highly absorbent resin as well as the deposition thereof inside the incinerator can be prevented during the incineration thereof.

It is an additional object of the invention to provide a disposal bag or packaging material for a highly absorbent resin or an absorbent article comprising the highly absorbent resin, whereby the melting and solidification of the highly absorbent resin as well as the deposition thereof inside the incinerator can be prevented during the incineration thereof.

It is a still additional object of the invention to provide a method for incinerating a highly absorbent resin or an absorbent article comprising the highly absorbent resin, wherein the method can prevent the melting and solidification of the highly absorbent resin or can prevent the deposition thereof inside the incinerator during incineration.

The inventors have found that specific metal compounds are effective in overcoming the problems relating to the incineration of highly absorbent resins as described above. Thus, the invention has been achieved. More specifically, the incineration of a highly absorbent resin together with specific polyvalent metal compounds can reduce the problems. Therefore, absorbent articles comprising the highly absorbent resin can be incinerated well, with no need of any sophisticated incinerator or any increase of maintenance labor, at incineration sites. Detailed description will now follow.

1. A highly absorbent resin comprising a polyvalent metal compound capable of preventing the melting and solidification of the highly absorbent resin and the deposition thereof on the wall of an incinerator during the incineration of the highly absorbent resin.
2. An absorbent article comprising a highly absorbent resin and a polyvalent metal compound capable of preventing the melting and solidification of the highly absorbent resin and the deposition thereof on the wall of an incinerator during the incineration of the absorbent article.
3. A disposal bag for the disposal of a highly absorbent resin or an absorbent article comprising a highly absorbent resin or a packaging material for wrapping a highly absorbent resin or an absorbent article comprising a highly absorbent resin, the disposal bag or the packaging material comprising a polyvalent metal compound capable of preventing the melting and solidification of the highly absorbent resin and the deposition thereof on the wall of an incinerator during the incineration of the disposal bag or the packaging material and its contents.

4. A package comprising a highly absorbent resin or an absorbent article comprising a highly absorbent resin, and a packaging material housing the highly absorbent resin or the absorbent article, wherein a polyvalent metal compound or a solution thereof capable of preventing the melting and solidification of the highly absorbent resin and the deposition thereof on the wall of an incinerator during the incineration of the highly absorbent resin is packed in the packaging material along with the highly absorbent resin or the absorbent article.

5. A method for incinerating and disposing a highly absorbent resin or an absorbent article comprising a highly absorbent resin, comprising adding a polyvalent metal compound or a solution thereof to prevent the melting and solidification of the highly absorbent resin and the deposition thereof in an incinerator during incineration and disposal.

DETAILED DESCRIPTION OF THE INVENTION

Figure 1:
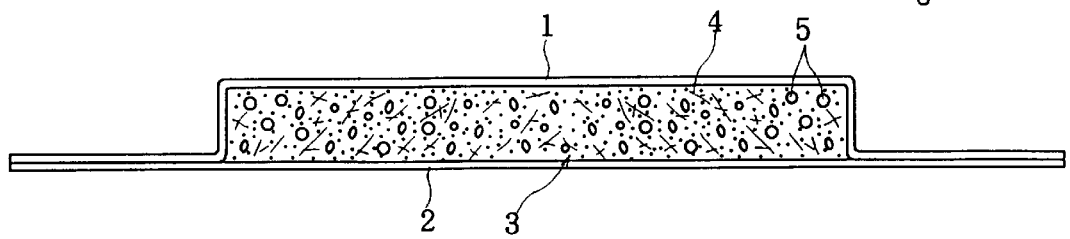
FIG. 1 is a cross-sectional view of a disposable diaper which is one example of the invention.

In accordance with the invention, the term highly absorbent resin includes all highly absorbent resins with the various potential problems as described above; more specifically, the term highly absorbent resin generally means a highly absorbent resin for use in producing absorbent articles such as disposable diaper, which includes, for example, high-molecular polymers such as polyacrylic acid and polysulfonic acid, copolymers thereof with vinyl alcohol, etc, graft polymers thereof with cellulose, starch, etc and carboxymethylated products, etc. Generally, these highly absorbent resins are in crosslinked structures and in the forms of alkali metal salts.

The aforementioned problems can be reduced when these highly absorbent resins are incinerated together with the polyvalent metal compounds according to the invention, whereby these highly absorbent resins can be incinerated well and can be disposed thereafter.

All polyvalent metal compounds with the effect of alleviating the abovementioned problems are in accordance with the invention, and specific preferable examples thereof are salts of aluminium, magnesium and calcium.

On the other hand, monovalent metal salts of lithium, sodium and potassium cannot overcome the various problems occurring during the incineration of highly absorbent resins, so these salts cannot be used. Further, use of hazardous heavy metals such as lead, tin, mercury and cadmium in the absorbent article for the invention is not recommended because such use is dangerous, and the ash after incineration might possibly be highly toxic.

When polyvalent metal compounds are used in accordance with the invention adding the above in solid or in solution immediately prior to or during incineration is possible; but preferably, the above is included beforehand in the highly absorbent resin or the absorbent article because no additional step is then needed during the incineration process.

Preferred is including polyvalent metal compounds in the composition of the garbage bag in which a highly absorbent resin or an absorbent article comprising the highly absorbent resin is placed after use and then incinerating the bag, as it is. Preference is also given to adding polyvalent metal compounds to a packaging material such as packaging sheet, container or the like for housing a highly absorbent resin or an absorbent article and incinerating the packaging material together with the highly absorbent resin or the absorbent article.

The mode of applying the invention to absorbent articles is specifically described below.

According to any one selected from the following processes, polyvalent metal compounds are used in the absorbent article.

1. Preliminarily mixing a polyvalent metal compound with a highly absorbent resin before constructing an absorbent article.
2. Preliminarily adding a polyvalent metal compound to the raw materials of a highly absorbent resin and then producing the highly absorbent resin.
3. Mixing a polyvalent metal compound with a highly absorbent resin when constructing an absorbent article
4. Independently adding a highly absorbent resin and a polyvalent metal compound when constructing an absorbent article.
5. Adding a polyvalent metal compound into elements of an absorbent article.

For each case, the most appropriate process should be selected from the above, depending on the type of the absorbent article to be produced, the production method, cost consideration, and the safety profile at production sites.

However, a polyvalent metal compound with high solubility in water may possibly inhibit the absorptivity of a highly absorbent resin. In such case, the polyvalent metal compound should never be in contact with fluids such as urine and menstrual blood so that they are not dissolved therein, thus avoiding the inhibition of the absorptivity of a highly absorbent resin. For this purpose, in other words, a polyvalent metal compound must be added beforehand into the elements of the absorbent article by kneading or other means or be covered or wrapped with liquid-impermeable materials. If the selected polyvalent metal compound is poorly soluble or insoluble in water, then of course, such consideration as described above are not required.

Additionally, some polyvalent metal compounds are acidic or alkaline, so depending on the acidity or alkalinity, such polyvalent metal compounds cause safety concern when used in the absorbent article. Even in such case, the polyvalent metal compounds should preliminarily be added into the elements of the absorbent article, and effects must be made to secure safe by. A polyvalent metal compound simply added to the elements may be present on the surface layer of the elements or may become dissociated from the elements, to cause safety problems in the elements per se. Hence, much attention should be paid to the process of adding a polyvalent metal compound. The safety profile can be determined, using as one indicator whether or not the absorbent article and the elements thereof can satisfy the voluntary standards of disposable diapers and the sanitary goods standards' section on Acids and Alkalis".

A polyvalent metal compound has no particular upper weight limit. Considerations of the cost and the weight increase of the resulting absorbent article should be allowed to determine the upper weight limit of the polyvalent metal compound on the other hand, a polyvalent metal compound of too little weight can not exhibit the desired effects upon incineration. Thus, the polyvalent metal compound in the highly absorbent resin is preferably 1% wt or more, more preferably 10% wt or more.

Figure 2:
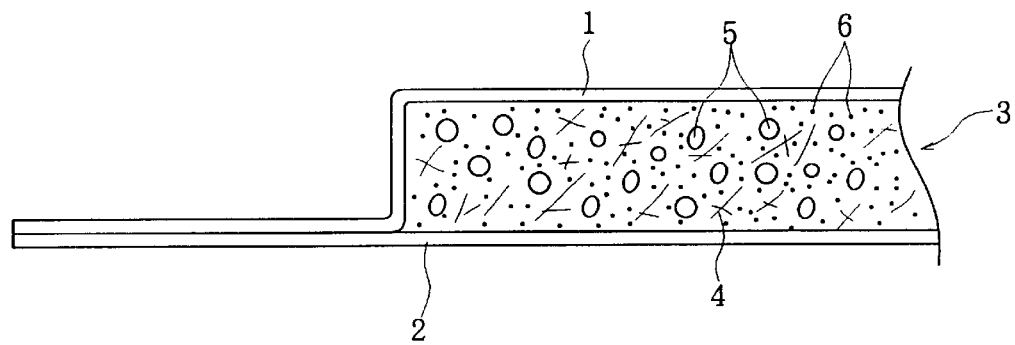
FIG. 2 is a partial cross-sectional view of a disposable diaper which is s another example of the invention.
Figure 3:
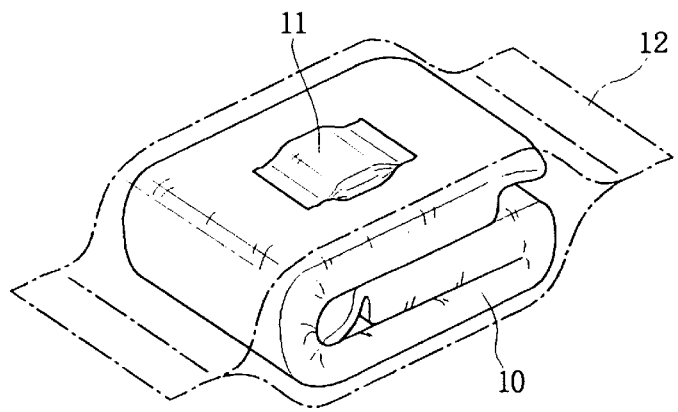
FIG. 3 is a perspective view of a disposable diaper package which is yet an additional example of the invention.

An embodiment of the invention will now be described in more detail in the following disposable diaper example containing a highly absorbent resin, with reference to drawings. FIG. 1 is a cross-sectional view of a disposable diaper that does not melt solidify during incineration; FIG. 2 is an partial cross-sectional view of a disposable diaper in which a polyvalent metal compound is.mixed with a highly absorbent resin; and FIG. 3 is a perspective view of a disposable diaper package. As shown in FIG. 1, the disposable diaper is composed of a liquid-permeable inner sheet 1, a liquid-impermeable outer sheet 2 and an absorbent core 3 interposed between the inner and outer sheets 1 and 2. The absorbent core 3 is prepared, for example, by wrapping with tissue paper, etc, absorbent fiber 4 in which highly absorbent resin 5 is dispersed.

1. The disposable diaper of FIG. 1 may be produced by adding a polyvalent metal compound during the process of producing highly absorbent resin 5 and subsequently using the resulting highly absorbent resin 5 containing the polyvalent metal compound. The highly absorbent resin 5 can prevent to a high degree of probability the generation of melt solidified by-products from the disposable diaper during incineration.
2. As shown in FIG. 2, the absorbent core 3 may be formed with the highly absorbent resin 5 and a polyvalent metal compound in a mixed state. A polyvalent metal compound in solid is first ground to powder or small granules (symbol 6 in FIG. 2); and the resulting polyvalent metal compound is dispersed, along with the highly absorbent resin 5, in the absorbent core 3.
3. In this case, the powder or granule polyvalent metal compound 6 in the absorbent core 3 is preferably arranged in the proximity to the region where the highly absorbent resin 5 is arranged.
4. A polyvalent metal compound may be contained in the liquid-impermeable sheet 2 composing the disposable diaper. In this case, the polyvalent metal compound contained in the liquid-impermeable sheet 2 is at 1% wt or more, preferably 10% wt or more relative to the highly absorbent resin 5 contained in the resulting disposable diaper, as described above. The liquid-impermeable sheet 2 is, for example, made of polypropylene or polyethylene. A polyvalent metal compound can be added to the raw materials of the sheet, so as to prepare a liquid-impermeable sheet 2 containing the polyvalent metal compound. Alternatively, a polyvalent metal compound may be arranged between the liquid-impermeable sheet 2 and the absorbent core 3 containing the highly absorbent resin 5.
5. As shown in FIG. 3, a conventional disposable diaper 10 containing a highly absorbent resin and a container 11 containing a polyvalent metal compound or a solution of a polyvalent metal compound may be both wrapped with a packaging material (or packaging sheet) 12 to prepare a packaged product. The container 11 for a solution of a polyvalent metal compound can be used in a simple manner, if the container 11 is of a spray type or tube type. Generally, plural disposable diapers are packed in one package for sale. A polyvalent metal compound at 1% wt or more, preferably 10% wt or more relative to the highly absorbent resin 5 contained in the plural disposable diapers, or a solution corresponding to the polyvalent metal compound, is placed in the container 11 and is then attached to the package. In another method, a polyvalent metal compound may be contained in a packaging material for packaging such disposable diaper. Alternatively, a garbage bag for the disposal of disposable diaper may contain the polyvalent metal compound.

The invention will now be described in the following examples. The advantages thereof can be demonstrated on comparison with comparative examples.

EXAMPLE

A highly absorbent resin (30 g) which is a sodium salt of a polyacrylate-crosslinked polymer (manufactured by Sanyo Chemical Industries, Co. Ltd.) was charged in 1.5 liters of water, to allow the highly absorbent resin to absorb water for 20 minutes. The resulting highly absorbent resin expanded after water absorption was dried at 105° C. for 20 hours into a mass. 5 g portions of the mass were taken, followed by addition of 1 g each of the following metal compounds to different portions; and the resulting mixtures were mildly blended together.

Example 1

Magnesium Oxide

Example 2

Magnesium Hydroxide

Example 3

Magnesium Silicate

Example 4

Aluminium Oxide

Example 5

Aluminium Hydroxide

Example 6

Aluminium Silicate

Comparative Example 1

No Salts Added

Comparative Example 2

Sodium Chloride

These mixtures were placed in porcelain crucibles and heated in a muffle furnace under gradual temperature elevation. The mixtures were heated at 600° C. for 30 minutes. Then, the temperature was further raised to 800° C. for 30 minutes for incineration.

After heating, the crucibles were taken out. The state of the inner face thereof was examined. In the individual examples, the resulting ash did not stick to the inner face of the crucibles, and 90% or more of the ash could be removed readily. In the individual comparative examples, 90% or more of the resulting ash stuck to the inner face of the crucibles, and the ash could not be removed. The aforementioned results indicate that the polyvalent metal compounds were sufficiently effective for the incineration of the highly absorbent resin.

The fundamental reason why the inventive advantage can be attained by the simultaneous incineration of the highly absorbent resin and the polyvalent metal compound has not yet been identified, but it is now hypothesized that any one or both of the following two principles may possibly function.

Possibility of melting point elevation

Many of alkali metal salts are at low melting points. The highly absorbent resin in accordance with the invention also belongs to the group of alkali metal salts. When aluminium is concurrently present with the salt of an alkali metal compound, for example sodium salt, aluminium attaches to the sodium salt, whereby the melting point is elevated Thus, the resulting sodium salt dose not readily melt solidify.

Possibility of the suppression of the deposition of melt product

The melting point of the polyvalent metal compound used in accordance with the invention is relatively high. Even if the highly absorbent resin is melted, therefore, the polyvalent metal compound not yet melted is still present between the molecules of the melted highly absorbent resin or between the melted highly absorbent resin and the incinerator wall or incinerator bottom, so that the solidification or deposition of the melted product is suppressed.

Based on these principles, in accordance with the invention, the solidification of a highly absorbent resin or the deposition thereof inside the incinerator can be prevented when a highly absorbent resin or an absorbent article containing a highly absorbent resin is incinerated. In accordance with the invention, from now on, wastes containing the highly absorbent resin can be incinerated well.

Therefore, the invention is applicable to highly absorbent resins and absorbent articles comprising the same. Such absorbent articles include: sanitary materials such as disposable diapers and sanitary napkin; agricultural and gardening materials such as water retentive materials for soil and seedling sheets; civil engineering materials and building materials such as dew preventive materials, soil bag and water shielding materials; cosmetics and pharmaceutical materials such as gel fragrance and gel poultice, etc. The invention is also applicable at incineration sites, namely plant sites for incinerating wastes in the production, hospital sites or sites of institutions for aged people where wastes are incinerated in an in-house manner, and incineration sites of industrial wastes and general wastes.

In the foregoing specification, the invention has been described in relation to preferred embodiments and many details have been set forth for the purpose of illustration. It will be apparent to those skilled in the art that the invention is susceptible to additional embodiments and that certain of the details described herein can be varied considerably without departing from the basic principles of the invention.

Further, 'comprises/comprising' when used in this specification is taken to specify the presence of stated features, integers, steps or components but does not preclude the presence or addition of one or more other features, integers, steps, components or groups thereof.

What is claimed is:

1. An absorbent article comprising:
   an absorbent core containing a highly absorbent resin; and
   a polyvalent metal compound which is present in the absorbent article separately and undissolved in the highly absorbent resin, and prevents melting, solidification and deposition of the highly absorbent resin on the wall of an incinerator during incineration of the absorbent article;
   wherein the separation of the polyvalent metal compound from the highly absorbent resin is established by one of:
   (a) grinding and dispersing the polyvalent metal compound while in solid form, along with the highly absorbent resin in the absorbent core and arranging the polyvalent metal compound proximally to the highly absorbent resin;
   (b) adding the polyvalent metal compound to an element of the absorbent article for containment therein to prevent the polyvalent metal compound from contacting liquid which is introduced into the absorbent article; and
   (c) covering or wrapping the polyvalent metal compound with a liquid-impermeable material such that the polyvalent metal compound is prevented from contacting liquid which is introduced into the absorbent article.

2. The absorbent article as set forth in claim 1, wherein the polyvalent metal compound is present in the absorbent article separately from the highly absorbent resin consistent with one of (b) and (c).

3. The absorbent article as set forth in claim 2, wherein the highly absorbent resin is crosslinked and in the form of alkali metal salt, and consists of at least one compound selected from the group consisting of: polyacrylic acid; polysulfonic acid; copolymer thereof with vinyl alcohol; graft polymer thereof with cellulose; graft polymer thereof with starch; and carboxymethylated product.

4. The absorbent article as set forth in claim 3, wherein the ratio of the polyvalent metal compound to the highly absorbent resin is at least 1% by weight.

5. The absorbent article as set forth in claim 4, wherein the polyvalent metal compound is at least one compound selected from the group consisting of aluminum salt, magnesium salt and calcium salt.

6. The absorbent article as set forth in claim 4, wherein the polyvalent metal compound is insoluble in water.

7. The absorbent article as set forth in claim 1, wherein the absorbent article is one of a disposable diaper and a sanitary napkin.

8. A disposal bag for disposal of an absorbent article comprising a highly absorbent resin, the disposal bag comprising a polyvalent metal compound which prevents the melting, solidification and deposition of the highly absorbent resin on the wall of an incinerator during the incineration of the disposal bag and contents therein, wherein the polyvalent metal compound is present in the disposable bag separately and undissolved in the highly absorbent resin.

9. The absorbent article as set forth in claim 8, wherein the absorbent article is one of a disposable diaper and a sanitary napkin.

10. The disposal bag as set forth in claim 8, wherein the highly absorbent resin is crosslinked structure and in the form of alkali metal salt, and consists of at least one compound selected from the group consisting of: polyacrylic acid; polysulfonic acid; copolymer thereof with vinyl alcohol; graft polymer thereof with cellulose; graft polymer thereof with starch; and carboxymethylated product.

11. The disposal bag as set forth in claim 10, wherein the ratio of the polyvalent metal compound to the highly absorbent resin is at least 1% by weight.

12. The disposal bag as set forth in claim 11, wherein the polyvalent metal compound is at least one compound selected from the group consisting of aluminum salt, magnesium salt and calcium salt.

13. The disposal bag as set forth in claim 11, wherein the polyvalent metal compound is insoluble in water.

14. A packaging material for wrapping an absorbent article comprising a highly absorbent resin, the packaging material comprising a polyvalent metal compound which prevents the melting, solidification and deposition of the highly absorbent resin on the wall of an incinerator during the incineration of the packaging material and contents therein, wherein the polyvalent metal compound is present in the packaging material separately and undissolved in the highly absorbent resin.

15. The packaging material as set forth in claim 14, wherein the absorbent article is one of a disposable diaper and a sanitary napkin.

16. The packaging material as set forth in claims 14, wherein
the highly absorbent resin is crosslinked and in the form of alkali metal salt, and consists of at least one compound selected from the group consisting of: polyacrylic acid; polysulfonic acid; copolymer thereof with vinyl alcohol; graft polymer thereof with cellulose; graft polymer thereof with starch; and carboxymethylated product.

17. The packaging material as set forth in claim 16, wherein
the ratio of the polyvalent metal compound to the highly absorbent resin is at least 1% by weight.

18. The packaging material as set forth in claim 17, wherein
the polyvalent metal compound is at least one compound selected from the group consisting of aluminum salt, magnesium salt and calcium salt.

19. The packaging material as set forth in claim 17, wherein
the polyvalent metal compound is insoluble in water.

20. A package comprising an absorbent article comprising a highly absorbent resin, and a packaging material housing the highly absorbent resin or the absorbent article, wherein a container containing a polyvalent metal compound or a solution thereof which prevents melting, solidification and deposition of the highly absorbent resin on a wall of an incinerator during incineration of the absorbent article is packed in the packaging material along with the absorbent article, wherein the polyvalent metal compound is present in the container separately and undissolved in the highly absorbent resin.

21. The package as set forth in claim 20, wherein the absorbent article is one of a disposable diaper and a sanitary napkin.

22. The package as set forth in claim 20, wherein
the highly absorbent resin is crosslinked and in the form of alkali metal salt, and consists of at least one compound selected from the group consisting of: polyacrylic acid; polysulfonic acid; copolymer thereof with vinyl alcohol; graft polymer thereof with cellulose; graft polymer thereof with starch; and carboxymethylated product.

23. The highly absorbent resin as set forth in claim 2, wherein
the ratio of the polyvalent metal compound to the highly absorbent resin is at least 1% by weight.

24. The package as set forth in claim 22, wherein
the ratio of the polyvalent metal compound to the highly absorbent resin is at least 1% by weight.

25. The package as set forth in claim 24, wherein
the polyvalent metal compound is at least one compound selected from the group consisting of aluminum salt, magnesium salt and calcium salt.

26. A package as set forth in claim 24, wherein
the polyvalent metal compound is insoluble in water.

* * * * *